(12) United States Patent
Yang et al.

(10) Patent No.: US 7,486,392 B2
(45) Date of Patent: Feb. 3, 2009

(54) METHOD OF INSPECTING FOR DEFECTS AND APPARATUS FOR PERFORMING THE METHOD

(75) Inventors: Yu-Sin Yang, Seoul (KR); Chung-Sam Jun, Suwon-si (KR); Ki-Suk Chung, Seoul (KR); Tae-Sung Kim, Suwon-si (KR); Byung-Sug Lee, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 107 days.

(21) Appl. No.: 11/476,651

(22) Filed: Jun. 29, 2006

(65) Prior Publication Data

US 2007/0002317 A1 Jan. 4, 2007

(30) Foreign Application Priority Data

Jun. 30, 2005 (KR) ............... 10-2005-0057450

(51) Int. Cl.
*G01N 21/00* (2006.01)
(52) U.S. Cl. ............... 356/237.2; 356/237.3; 356/237.4
(58) Field of Classification Search ............... None
See application file for complete search history.

(56) References Cited

U.S. PATENT DOCUMENTS 5,604,585 A * 2/1997 Johnson et al. .......... 356/237.5

2005/0248756 A1 * 11/2005 Lin et al. ............... 356/237.4

FOREIGN PATENT DOCUMENTS

| JP | 09-061344 | 3/1997 |
| JP | 09-203621 | 8/1997 |
| JP | 10-185535 | 7/1998 |
| KR | 1995-0006428 | 3/1995 |
| KR | 2001-0053397 | 6/2001 |
| KR | 1020020021062 A | 3/2002 |
| KR | 1020040062299 A | 7/2004 |

* cited by examiner

*Primary Examiner*—Michael P Stafira
(74) *Attorney, Agent, or Firm*—Volentine & Whitt, PLLC

(57) ABSTRACT

In a method of inspecting an object, a first light is irradiated onto a bare object and a first reflection signal is reflected from the bare object. A second light is irradiated onto a processed object and a second reflection signal is reflected from the processed object. The first and second reflection signals are differentiated, to thereby generate respective first and second differential signals. A defect on the processed object is detected by a comparison between the first and second differential signals. The first and second differential signals overlap with each other and at least one signal-deviation portion is detected. The first and second differential signals are spaced apart out of an allowable error range in the signal-deviation portion. The defect is detected from a portion of the processed object corresponding to the signal-deviation portion.

11 Claims, 7 Drawing Sheets

METHOD OF INSPECTING FOR DEFECTS AND APPARATUS FOR PERFORMING THE METHOD

BACKGROUND OF THE INVENTION

1. Field of the Invention

Example embodiments of the present invention relate to a method of inspecting defects and an apparatus for performing the same method, and more particularly, to a method of inspecting semiconductor processing defects, such as particles and scratches, and to an apparatus for performing the method.

A claim of priority is made to Korean Patent Application No. 2005-57450 filed on Jun. 30, 2005, the content of which is herein incorporated by reference in its entirety.

2. Description of the Related Art

The high integration degree and the high performance of semiconductor devices necessitate an inspection process for detecting various processing defects on a semiconductor wafer. As examples, processing defects include particles on a wafer, and bridge failures and structural collapses generated during patterning processes. As another example, processing defects include scratches generated on the surface of a wafer during a chemical mechanical polishing (CMP) process. A defect inspection process includes inspecting the processing defects and determining what effect the defects may have on a wafer in a subsequent process.

In general, defect inspection processes are largely classified into dark-field inspection processes based on a light scattering theory, and bright-field inspection processes based on a high-speed microscope theory. Both the conventional dark-field inspection process and the conventional bright-field inspection process compare image data to detect for processing defects, where the image data corresponds to dies on a semiconductor substrate. Neighboring dies adjacent to each other are required to be substantially identical on a semiconductor substrate. Therefore, differences between the image data of the neighboring dies indicate that processing defects exist in the neighboring dies on the substrate.

A die on a semiconductor substrate generally has a complicated structure, including a cell structure, a peripheral structure, a sense amplifier (SA) and a sub-word divider (SWD), and thus the neighboring dies on the substrate are difficult to compare with each other. As a result, comparison of the neighboring dies requires high-quality measurement equipment. In particular, both the conventional dark-field inspection process and the conventional bright-field inspection process require advanced optical equipment and calculation equipment.

FIG. 1 is a flow chart showing a conventional method of inspecting for processing defects. In particular, the flow chart in FIG. 1 shows an operational sequence for detecting processing defects on a wafer during a manufacturing process for a semiconductor device.

Referring to FIG. 1, an inspection wafer, which is randomly selected among to-be-inspected wafers, is loaded into a detection apparatus for detecting processing defects on the wafer (step S11), and a laser is irradiated onto the wafer (step S12). The irradiated laser is reflected from the wafer (step S13), and the reflected laser is focused into a photo multiplier tube (step S14). The photo multiplier tube calculates an optimal amplification ratio in accordance with an intensity of the reflected laser (step S15). The reflected laser is amplified in accordance with the optimal amplification ratio (step S16). The amplified laser is transformed into a digital signal (step S17), and the digital signal is stored into a server (step S18). Then, the digital signal is compared with a reference signal that is obtained from a reference wafer, and the detection apparatus provides information as to whether or not the inspection wafer includes a processing defect (step S19).

Various minute structures such as a line, a spacer, a contact hole and a pattern are formed on a corresponding region of a wafer such as a cell region, a peripheral region, an SA region and an SWD region. A reflectivity of the minute structure is substantially the same in the same region, but is different from that in another region. That is, the reflectivity of the minute structure is varied in accordance with each region of the wafer. Accordingly, when the reflection laser is amplified at the same amplification ratio regardless of each region of the wafer, the image data measured from each region of the wafer is also different from one another in accordance with each region of the wafer. As a result, the difference between the measured image data does not provide any information on the existence of the defect on the wafer. For the above reasons, high-quality and advanced optical equipment and calculation equipment are required for detecting processing defects using the comparison of the measured image data. Such high-quality and advanced optical equipment and calculation equipment are expensive, and generally a long time is needed to detect for processing defects. That is, a large amount of image data is compared with one another during the detection process, and as a result the conventional detection of processing defects consumes a lot of time even when sophisticated and expensive detection equipment is utilized.

Japanese Laid-Open Patent Publication 1997-203621 discloses a method of inspecting pattern defects, a method of evaluating a process for manufacturing a semiconductor using the same, and a method of adjusting positions of a plurality of image data. Japanese Laid-Open Patent Publication 1998-185535 discloses a system for manufacturing semiconductor devices and a method of inspecting processing defects.

According to the above patent publications, a light is irradiated onto an inspection wafer on which a unit process for manufacturing a semiconductor device is performed, and a reflected light reflected from the wafer is filtered and detected through a complicated optical unit. Image data regarding the inspection wafer is measured by processing the detected reflected light. The measured image data is differentiated with reference to time, and the differentiated imaged data is compared with reference image data. A plurality of actual wafers undergoes the same process as conducted on the inspection wafer, and the processing defects on the actual wafers are detected by naked-eye inspection equipment, such as a microscope and a scanning electron microscope (SEM). One of the actual wafers satisfying a given defect standard is selected as the reference wafer and the reference image data is obtained from the reference wafer.

The above patent publications, each of the measured image data is compared with the reference image data for detecting the processing defects and as a result, detection efficiency is not sufficiently improved. In addition, high cost equipment is utilized and a long time is need to obtain the reference image data.

In the past, only several tens of the processing defects were typically detected on a semiconductor wafer. More recently, however, several hundreds or several thousands of the processing defects are typically being detected on a semiconductor wafer due to the high integration degrees thereof. However, the development of inspection methods and apparatus has not been able to keep pace with that of the semiconductor device, so that the costs and time for detecting for processing defects, thus reducing manufacturing throughput.

SUMMARY OF THE INVENTION

Example embodiments of the present invention provide a method of inspecting for processing defects on an inspection object.

Example embodiments of the present invention also provide an apparatus for performing the above method.

According to an aspect of the present invention, there is provided a method of inspecting an object. A first light is irradiated onto a bare object, and a first reflection signal is reflected from the bare object. The bare object includes no structures thereon. A predetermined process is performed on the bare object, so that a predetermined structure is formed on the bare object. A second light is irradiated onto the processed object, and a second reflection signal is reflected from the processed object. First and second differential signals are generated by differentiating the first and second reflection signals, respectively. A processing defect is detected on the processed object by a comparison between the first and second differential signals. As an example embodiment of the present invention, the first and second differential signals overlap with each other, and at least one signal-deviation portion is detected from the overlapped differential signals. The first and second differential signals are spaced apart out of an allowable error range in the signal-deviation portion. A portion of the processed object is located correspondently to the signal-deviation portion and the processing defect is detected from the portion of the processed object corresponding to the signal-deviation portion. In an example embodiment of the present invention, the first and second differential signals are aligned with each other on a basis of peak points of the first and second differential signals. The peak points are substantially identical to one another in the first and second differential signals. In an example embodiment of the present invention, the reflection signal includes an intensity of the first reflected light and the second reflection signal includes an intensity of the second reflected light. In an example embodiment of the present invention, the first and second lights have the same incident angle with respect to the bare substrate and the processed object, respectively, and the incident angle is in a range from about 10° to about 90° with respect to a surface of the processed object. In an example embodiment of the present invention, the object includes a semiconductor substrate and processing the object includes forming a minute structure on the semiconductor substrate.

According to another aspect of the present invention, there is provided an apparatus for inspecting an object, which includes a light source, a light receiver, a differentiation operator and a detector. The light source irradiates a first light onto a bare object and a second light onto a processed object, respectively. The bare object includes no structures thereon and the processed object includes a structure thereon. The light receiver receives first and second reflection signals reflected from the bare object and the processed object, respectively. The differentiation operator generates first and second differential signals by differentiating the respective first and second reflection signals. The detector detects a processing defect on the processed object by a comparison between the first and second differential signals. In an example embodiment of the present invention, the detector includes first, second, third and fourth processing modules. The first processing module detects peak points in the first and second differential signals, and the peak points are substantially identical to one another in the first and second differential signals. The second processing module overlaps the first and second differential signals on a basis of the detected peak points, and the third processing module detects at least one signal-deviation portion in which the first and second differential signals are spaced apart out of an allowable error range. The fourth processing module locates a portion of the processed object corresponding to the signal-deviation portion. In an example embodiment of the present invention, the inspection apparatus may further include a memory unit for storing the first and second differential signals. In an example embodiment of the present invention, the light source and the light receiver positions are parallel with each other in a direction vertical to the object, so that the first and second lights are vertically irradiated onto the bare and processed objects, respectively, and the first and second reflection signals are also vertically received into the light receiver, respectively. In an example embodiment of the present invention, the light receiver includes a photo multiplier tube, a photodiode, a phototransistor and a photoelectric tube. In an example embodiment of the present invention, the object includes a semiconductor substrate includes a plurality of dies.

According to embodiments of the present invention, the processing defect may be detected from the processed object without an image of the processed object. In addition, the inspection apparatus may only utilizes the reflected light that is reflected from the processed substrate at a reflection angle substantially identical to an incident angle except for the light scattered from the processed substrate, so that the inspection process may be performed in a shorter time period. As a result, the processed wafer may be inspected with high efficiency and with high reliability.

BRIEF DESCRIPTION OF THE DRAWINGS

The above and other features and advantages of the present invention will become readily apparent by reference to the following detailed description when considering in conjunction with the accompanying drawings, in which.

DESCRIPTION OF THE EMBODIMENTS

Figure 1:
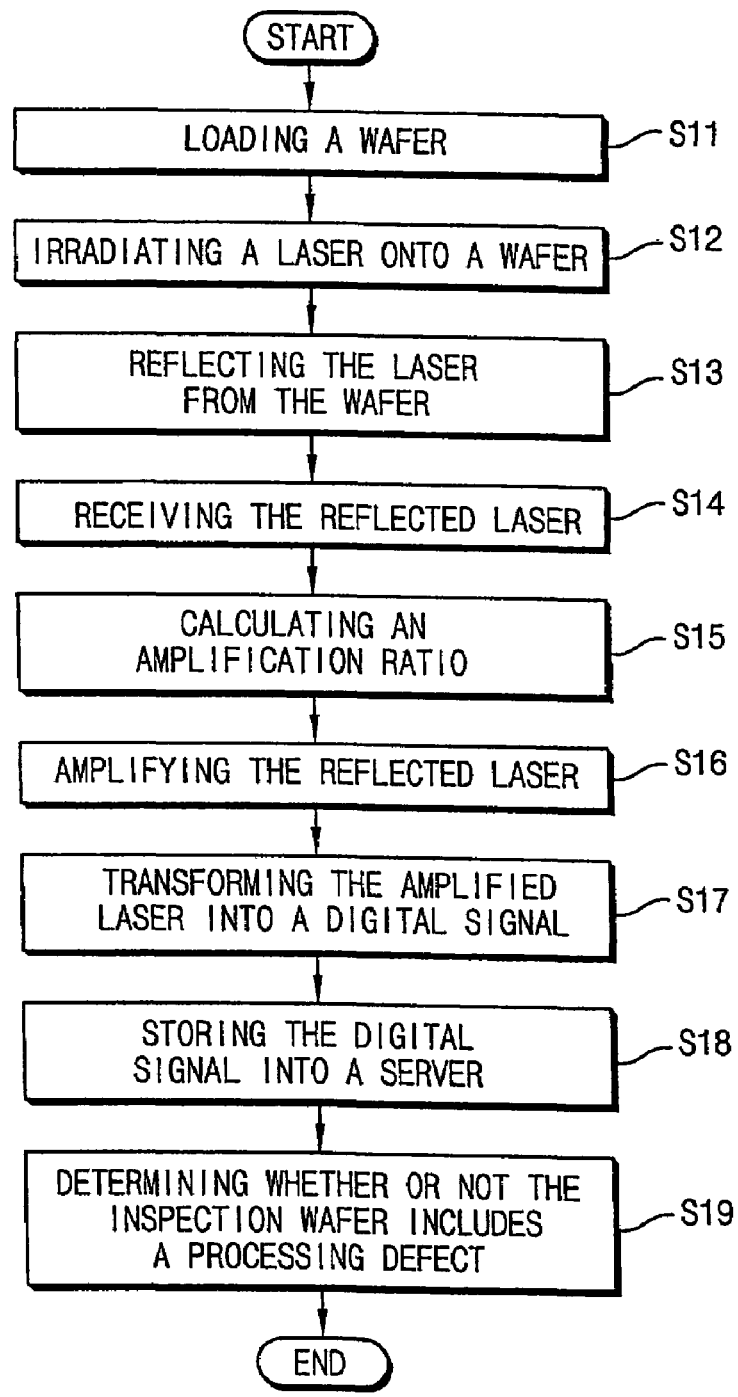
FIG. 1 is a flow chart for explaining a conventional method of inspecting processing defects.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
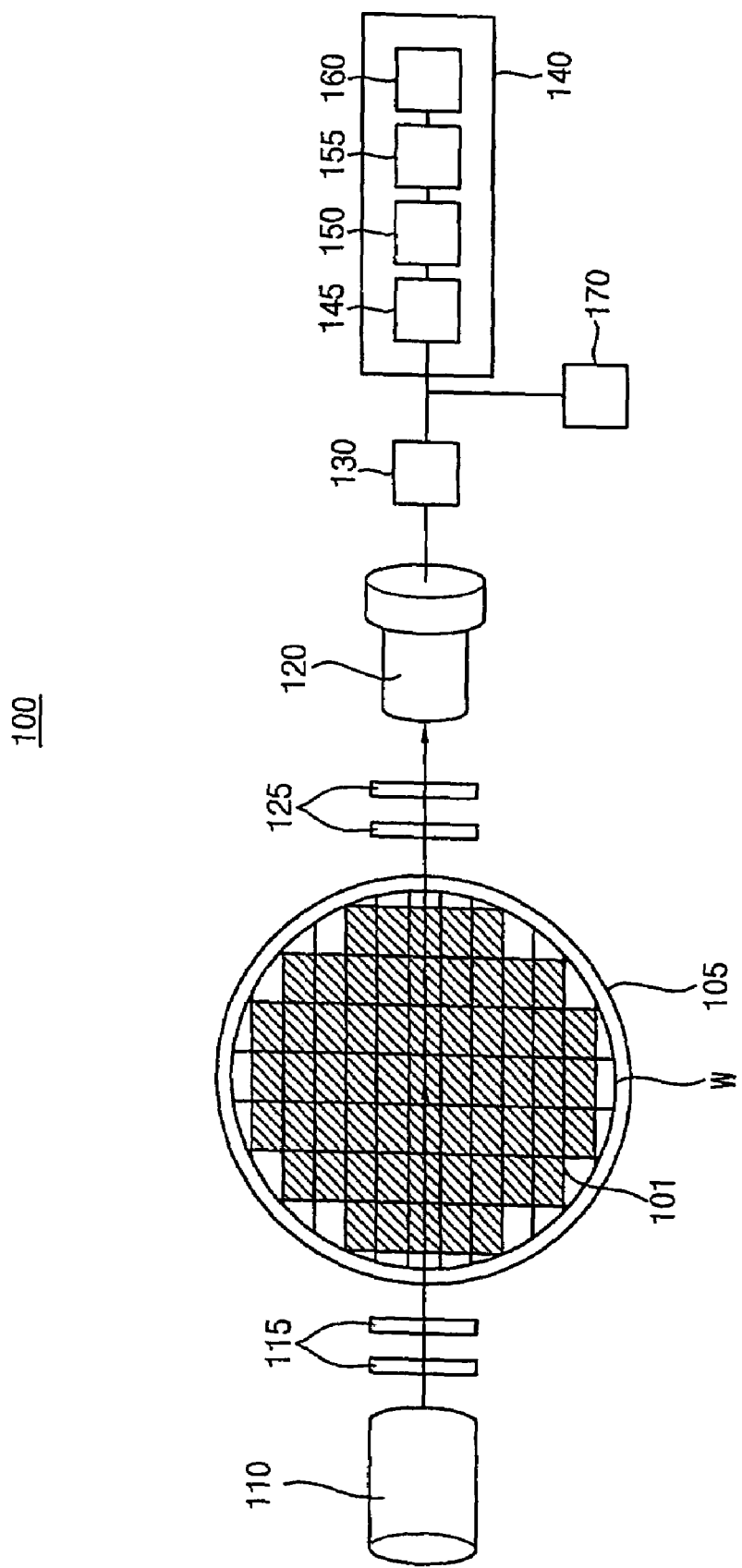
FIG. 2 is a structural view illustrating an inspection apparatus for inspecting processing defects on an inspection wafer in accordance with an example embodiment of the present invention.

FIG. 2 is a structural view illustrating an inspection apparatus for inspecting processing defects on an inspection wafer in accordance with an example embodiment of the present invention.

Referring to FIG. 2, the inspection apparatus 100 includes a light source 110, a light receiver 120, a differentiating operator 130 and a detector 140. The detector 140 includes first, second, third and fourth processing modules 145, 150, 155 and 160.

An inspection object such as a semiconductor wafer W, which is to be inspected for detecting processing defects on the inspection object, is positioned on the stage 105. The stage 105 may support the wafer W and may horizontally move the wafer W.

Various minute structures for a memory device or a non-memory device are repeatedly or non-repeatedly formed on the wafer through unit processes for manufacturing a semiconductor device. For example, when a memory chip is formed on the wafer, a die 101 includes a plurality of cell structures that are repeatedly formed on about 70% to about 80% of the die 101, and peripheral structures, a sense amplifier (SA) and a sub-word divider (SWD) that are non-repeatedly formed on about 20% to about 30% of the die 101. For example, when a non-memory chip or a system-on-chip (SOC) is formed on the wafer, a static random-access memory (SRAM), a dynamic random-access memory (DRAM), a logic circuit or a flash memory is non-repeatedly formed on the die 101. A plurality of cells is also repeatedly formed in each of the SRAM region, the DRAM region and the flash memory region. That is, both the memory chip and the non-memory chip includes a repetition region in which the minute structures are repeatedly formed and a non-repetition region in which the minute structures are non-repeatedly formed. The minute structures may be formed at various pitches in the repetition region and the non-repetition region. The light source 110 is arranged over the stage 105 on which the wafer is positioned.

The light source 110 generates light that is to be irradiated onto the wafer W. The light irradiated from the light source 110 may include, for example, a green light having a wavelength of about 500 nm to about 600 nm, a white light (WL) having a wavelength of about 365 nm to about 600 nm, a broadband-ultraviolet (BBUV) light having a wavelength of about 350 nm to about 450 nm, a longwave-ultraviolet (LUV) light having a wavelength of about 365 nm, a deep-ultraviolet (DUV) light having a wavelength of about 300 nm to about 100 nm or an extreme-ultraviolet (EUV) light having a wavelength of no more than about 100 nm. The light is then continuously scanned on the wafer W. As an example embodiment of the present invention, the light may be irradiated onto the wafer W through a first optical member 115.

The first optical member 115 is arranged between the light source 110 and the stage 105, and improves optical characteristics of the light by, for example, filtering the light into a predetermined wavelength. As an example embodiment of the present invention, the first optical member 105 includes a polarization plate and an aperture. In addition, a path alteration member (not shown) such as a mirror and a prism may be further arranged between the first optical member 105 and the wafer W.

The light may be irradiated onto the wafer W at various incident angles. For example, the light may be irradiated onto the wafer W at an incident angle of about 10° to about 90°. In the present embodiment of the invention, the light is irradiated onto the wafer W vertically (that is, at an incident angle of about 90°).

The light irradiated onto the wafer W is reflected from the wafer W in accordance with a shape and a position of the minute structure on the wafer W. As a result, when the wafer W includes processing defects such as a particle and a microscratch, the reflected light includes some information about the processing defects on the wafer W. The reflected light is received by the light receiver 120. As an example embodiment of the present invention, the light receiver 120 may be arranged in such a way that the reflected light having a reflection angle which is the same as the incident angle is only received by the receiver 120 so as to improve an inspection efficiency.

The light receiver 120 generates a voltage in proportion to an intensity of the reflected light, and includes a photo multiplier tube (PMT), a photo diode, a photo transistor and a photoelectric tube. A second optical member 125 may be further arranged between the wafer W and the stage 105, thereby removing noise from the reflected light before the reflected light reaches the light receiver 120. As an example embodiment of the present invention, the second optical member includes a polarization plate and an aperture.

The reflected light has very weak light intensity and is amplified in the light receiver 120. An amplification ratio of the reflected light is determined by a voltage applied to the light receiver 120. The light receiver 120 generates photo electrons in accordance with the amplified intensity of the reflected light, thereby generating a photoelectric current.

As a result, the photoelectric current generated from the light receiver 120 reflects information on the light intensity of the reflected light.

The light is continuously irradiated onto the wafer W when scanning the wafer W using the light, and is continuously reflected from the wafer W. As a result, the light receiver 120 continuously receives the reflected light, so that the photoelectric current is continuously generated from the light receiver 120. That is, the photoelectric current continuously varies in accordance with the intensity of the reflected light. Accordingly, the variation of the photoelectric current indicates the intensity variation of the reflected light, and the photoelectric current functions as a reflection signal indicating the intensity of the reflected light. As an example embodiment of the present invention, the intensity of the reflected light may be represented as an absolute unit, such as a reflectance.

Optical characteristics of the reflected light may be varied in accordance with physical characteristics of a layer on the wafer W, a minute structure on the layer and processing defects in the layer and the minute structure. According to an optical theory, when a light is irradiated onto an inspection object at an incident angle, the light is reflected from the inspection object at a reflection angle substantially identical to the incident angle. However, when fine particles are located on the inspection object, the incident light is scattered by the fine particles, so that the intensity of the reflected light is varied by the particles on the inspection object. The intensity of the reflected light is theoretically expressed as the following equation (1) on condition that the particle is a sphere.

$$I_R = \frac{8\pi^4 a^6}{\lambda^4 R^4} \left| \frac{n^2 - 1}{n^2 + 2} \right|^2 (1 + \cos^2\theta) I_i \qquad (1)$$

In equation (1), $I_i$ denotes an intensity of the incident light, $I_R$ denotes an intensity of a reflected light, $\lambda$ denotes a wavelength of the incident light, n denotes a refractive index of the particle, R denotes a distance of a path of the reflected light (that is, a distance between the inspection object and the light receiver), a denotes a diameter of the particle and $\theta$ denotes an incident angle of the incident light.

Equation (1) indicates that the intensity of the reflected light may be varied in accordance with the physical characteristics of a layer on the wafer W, the minute structure on the layer and processing defects in the layer and the minute structure. Accordingly, the reflection signal generated from the light receiver 120 may provide some information on the characteristics of the layer on the wafer W, the minute structure and the processing defects. The reflection signal is supplied into the differentiating operator 130.

The differentiating operator 130 generates an output function in proportion to a rate of change of an input function. That is, the differentiating operator 130 differentiates the reflection signal to generate a differential signal. As an example embodiment of the present invention, the differentiating operator 130 includes a differentiating circuit as shown in FIG. 3.

Figure 3:
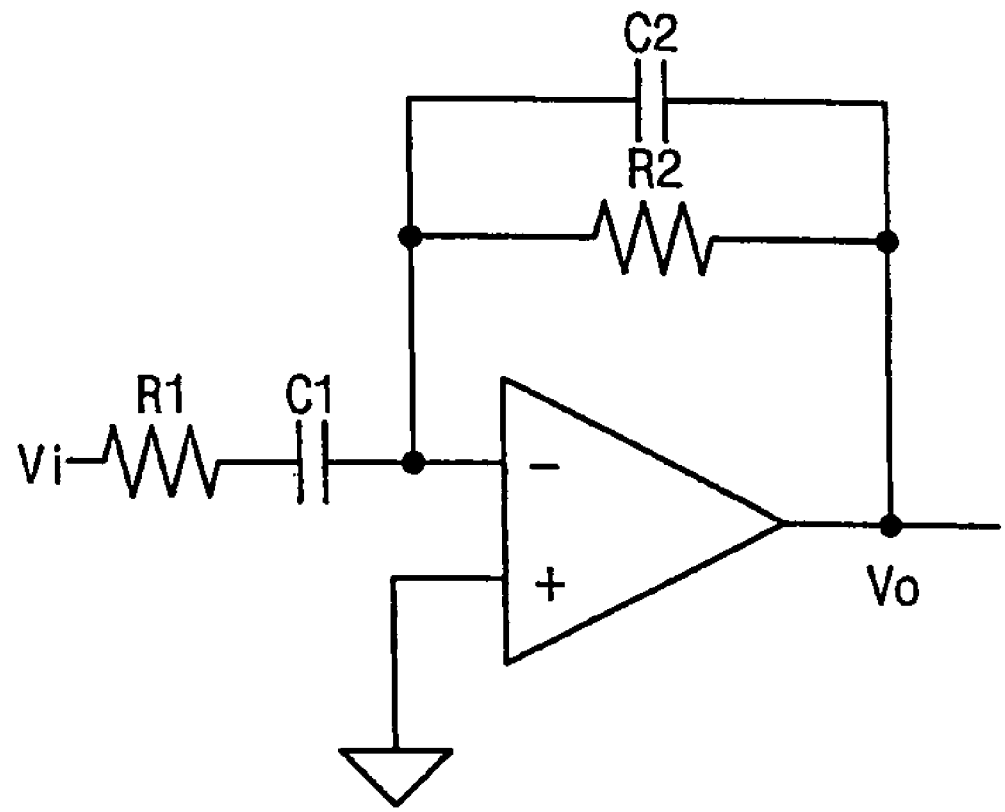
FIG. 3 is a circuit diagram illustrating a differentiating operator shown in FIG. 2.

FIG. 3 is a circuit diagram illustrating a differentiating operator shown in FIG. 2. While the present embodiment discloses an analog circuit as the differentiating operator such as the circuit diagram in FIG. 3, one of ordinary skill in the art will understand that a digital circuit may also be utilized as the differentiating operator so as to perform a more accurate differentiating operation. The circuit diagram in FIG. 3 is merely illustrated for the sake of convenient explanation of the differentiating operator 130, and thus the differentiating operator 130 should not be limited to the analog circuit shown in FIG. 3. Rather, various changes and modifications to the differentiating operator 130 can be made by one skilled in the art.

In FIG. 3, $V_i$ denotes an input voltage, $R_1$ denotes a serial resistance, $R_2$ denotes a feedback resistance, $C_1$ denotes an input condenser and $C_2$ denotes a parallel condenser. An output voltage $V_o$ of the differentiating operator 130 is expressed as the following equation (2).

$$V_o = \frac{V_i R_2}{\left(R_1 + \dfrac{1}{sC_1}\right)(1 + sC_2 R_2)} \qquad (2)$$

The differentiating operator is characterized in that an input frequency is proportional to a gain. When a capacitance of the parallel condenser $C_2$ is zero, a maximum gain of the differentiating operator is limited to the value of $$\frac{R_2}{R_1}.$$

That is, the gain is proportional to a first frequency within a preset frequency, and is not increased beyond the preset frequency. The first frequency $f_1$ is expressed as the following equation (3).

$$f_1 = \frac{1}{R_1 C_1} \quad (3)$$

In addition, when the gain needs to be reduced at a sufficiently high frequency, an integration process is performed by the parallel condenser $C_2$, so that the gain is reversely proportional to a second frequency beyond the preset frequency. The second frequency $f_2$ is expressed as the following equation (4).

$$f_2 = \frac{1}{R_2 C_2} \quad (4)$$

The first and second frequencies $f_1$ and $f_2$ may have various values. When the second frequency $f_2$ is higher than the first frequency $f_1$, the differentiating operator 130 differentiates the photoelectric current having a relatively lower frequency and integrates the photoelectric current having a relatively higher frequency.

According to the above characteristics of the differentiating operator, the differential signal of a reference value is generated from the differentiating operator 130 in that case that the reflection signal has a substantially constant frequency such as a stepped signal. In addition, when the reflection signal is varied out of an allowable frequency range, the differentiating operator 130 generates the differential signal corresponding to a rate of a change of the reflection signal. The differential signal is supplied to the detector 140.

The detector 140 analyzes the differential signal provided from the differentiating operator 130, thereby detecting processing defects on the wafer W. As an example embodiment of the present invention, the detector 140 includes the first, second, third and fourth processing modules 145, 150, 155 and 160. The first processing module 145 causes all of the peak points of each differential signal, which are substantially identical among one another, to have the same alignment value, thereby aligning the differential signals with respect to the alignment value. The second processing module 150 overlaps a plurality of the aligned differential signals with one another. The third processing module 155 detects at least one signal-deviation portion in which the first and second differential signals are not overlapped, or are spaced apart beyond an allowable error range. The fourth processing module 160 locates a portion of the wafer W corresponding to the detected signal-deviation portion of the overlapped differential signals.

A reference differential signal is stored into a memory unit 170, and the differential signal generated from the differentiating operator 130 is supplied into the first processing module 145. Hereinafter, the reference differential signal is referred to as a first differential signal and the differential signal generated from the differentiating operator 130 is referred to as a second differential signal. The first processing module 145 extracts all the peak points that are substantially identical in both the first and second differential signals. The first differential signal may be generated by processing a reflected light that is reflected from a bare wafer without any layer thereon. That is, the first differential signal is generated by processing a reflected light that is reflected from the bare wafer before a deposition process for forming the thin layer on the wafer, and the second differential signal is generated by processing a reflected light that is reflected from the wafer including the thin layer after the deposition process. Besides the deposition process for forming a thin layer on the wafer, the first differential signal may be generated from a wafer before a photolithography process, an etching process, a diffusion process or an ion implantation process may be performed on the wafer, and the second differential signal may be generated from the wafer after a photolithography process, an etching process, a diffusion process or an ion implantation process may be performed on the wafer.

The first and second differential signals are generated from the same wafer W, and accordingly the first and second differential signals are changed in substantially the same way. For example, a boundary area of the die 101 still remains substantially unchanged before and after a predetermined process performed on the wafer W, so that both the first and second differential signals have information regarding the boundary of the die 101. That is, the peak points indicating a reflectance change at the boundary area of the die 101 are included in the first and second differential signals. Likewise, the reflectance is also changed at a boundary area of a cell region in the die 101, so that the first and second differential signals include the same peak points indicating the change of the reflectance at the boundary area of the cell region in the die 101.

The first and second differential signals overlap with each other in the second processing module 150 on the basis of the peak points commonly shared by the first and second differential signals. As a result, the first differential signal, which is generated from the substrate before a process, and the second differential signal, which is generated from the substrate after a process, are aligned with each other in the second processing module 150.

The third processing module 155 detects a signal-deviation portion at which the first and second differential signals are not aligned, or spaced apart out of an allowable error range. The first differential signal is subtracted from the second differential signal at the signal portion, thereby generating a difference signal corresponding to the subtraction of the second differential signal from the first differential signal. Accordingly, the difference signal indicates a differential signal corresponding to a structure formed by a semiconductor process on the previously bare substrate. For example, the structure formed by a semiconductor process includes various minute structures, patterns, thin layers and defects on the bare substrate. The above structures excluding the defects are repeatedly formed on the bare substrate with some regularity. Accordingly, repeated peak points with some regularity in the difference signal indicate that the structures are non-defectively formed on the bare substrate, and irregular peak points in the difference signal indicate that the structures are defectively formed on the bare substrate. That is, the irregular peak points in the difference signal provide some information about the defects in the structures. As a result, the third processing module 155 detects the signal-deviation portion in which the first and second differential signals are not aligned with each other and most probably expected to include the irregular peak points.

The fourth processing module 160 locates a defective portion of the wafer W corresponding to the detected signal-deviation portion of the overlapped differential signals. As an example embodiment of the present invention, the difference signal is detected with reference to a coordinate system on the wafer W in the fourth processing module 160, so that the defective portion is definitely located with reference to the above coordinate system.

When the defective portion of the wafer W is located by the fourth processing module 160, an inspection apparatus such as a microscope and a scanning electron microscope (SEM) is used to re-inspect the defective portion of the wafer W to confirm whether or not the defective portion of the wafer W actually includes some defects. Hereinafter, a method of inspecting for defects on the wafer using the above inspection apparatus 100 will be described with reference to FIGS. 2 and 4.

Figure 4:
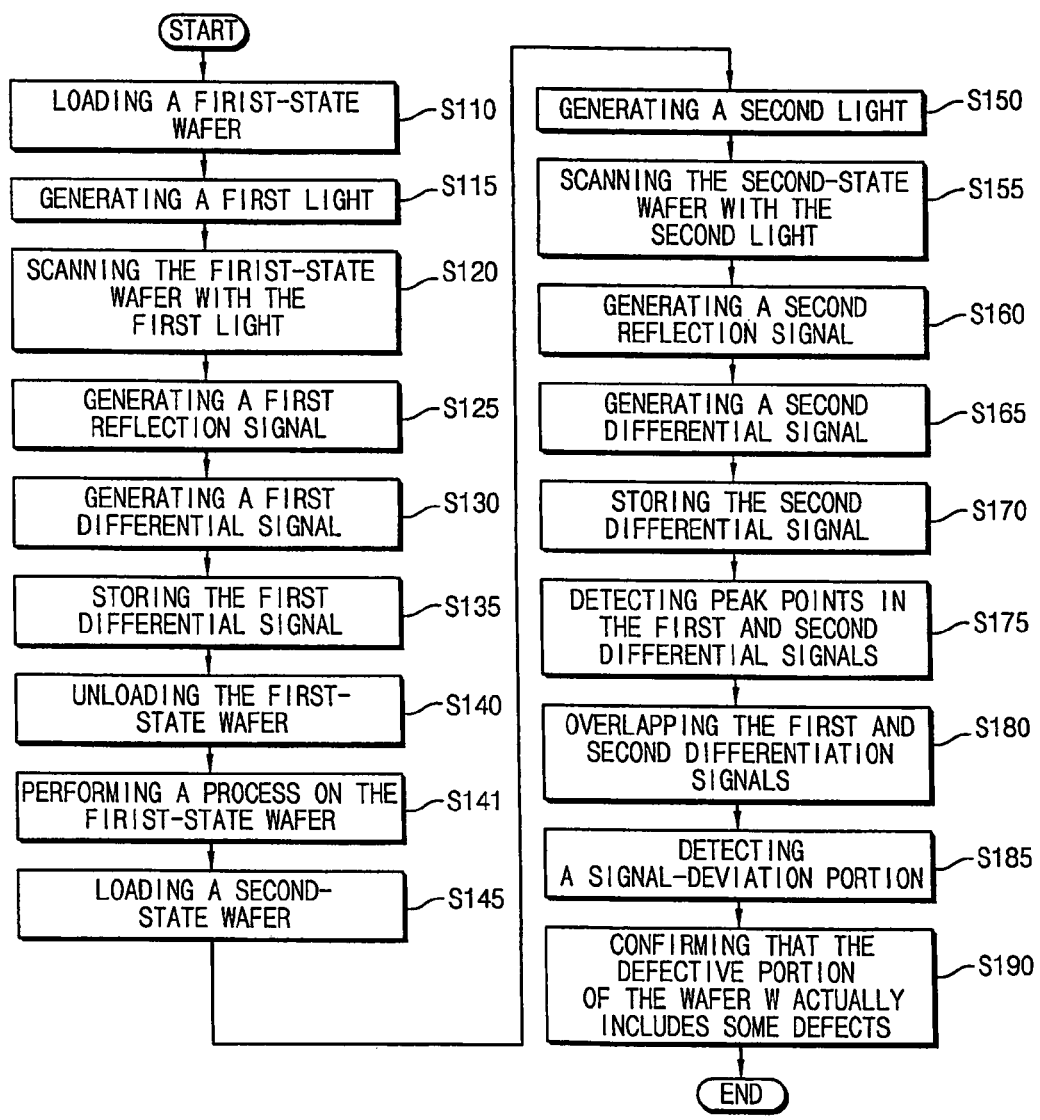
FIG. 4 is a flow chart for explaining a method of inspecting processing defects in accordance with an example embodiment of the present invention.

FIG. 4 is a flow chart for explaining a method of inspecting for processing defects in accordance with an example embodiment of the present invention.

Referring to FIGS. 2 and 4, a first-state wafer W is loaded into the inspection apparatus 100 (step S100). The first-state wafer W indicates a bare wafer on which no unit processes for manufacturing a semiconductor device are performed. A first light is generated from the light source 110 (step S115), and scans the entire surface of the first-state wafer W (step S120). The first light is reflected from the first-state wafer W, and the first reflected light is received and processed, to thereby generate a first reflection signal in the light receiver 120 (step S125). The first reflection signal is differentiated to generate a first differential signal (step S130). The first differential signal is stored into a memory unit 170 (step S135). The first-state wafer W is unloaded from the inspection apparatus 100, and a predetermined unit process for manufacturing a semiconductor device is performed on the first-state wafer W. Accordingly, the first-state wafer W is transformed into a second-state wafer W by the unit process (step S141). The second-state wafer W indicates a processed wafer on which a unit process for manufacturing a semiconductor device is performed, so that the second state is different from the first state in the same wafer W. The second-state wafer W is then loaded into the inspection apparatus 100 (step S145), and a second light is generated from the light source 110 (step S150). The second light scans the whole surface of the second-state wafer W (step S155). As an example embodiment of the present invention, the second light may be identical to the first light and may be irradiated onto the second-state wafer W at the same incident angle of the first light. The incident angle of the first and second lights may be varied at an angle of about 10° to about 90° with respect to the top surface of the first- and second-state wafers W, respectively. The second light is then reflected from the second-state wafer W, and the second reflected light is received and processed, to thereby generate a second reflection signal in the light receiver 120 (step S160). The second reflection signal is also differentiated to generate a second differential signal (step S165). The second differential signal is stored into the memory unit 170 (step S170). The peak points, which are substantially identical to one another, in the first and second differential signals, are detected (step S175), and the first and second differential signals are overlapped with each other on the basis of the peak points in the detector 140 (step S180). Then, the signal-deviation portion in which the first and second differential signals are not overlapped, or spaced apart out of an allowable error range, is detected (step S185), and a defective portion of the second-state wafer W, which corresponds to the detected signal-deviation portion of the overlapped differential signals, is located and re-inspected to confirm whether or not the defective portion of the wafer W actually includes some defects (step S190).

Figure 5:
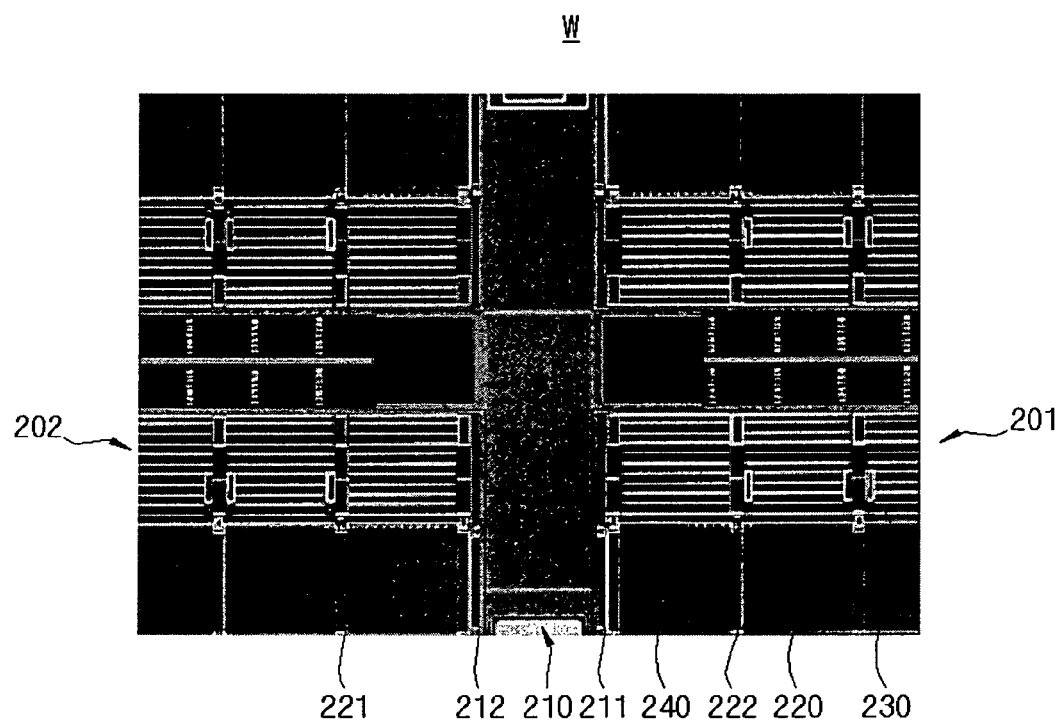
FIG. 5 is an enlarged picture showing a portion of the substrate in FIG. 2.
Figure 6:
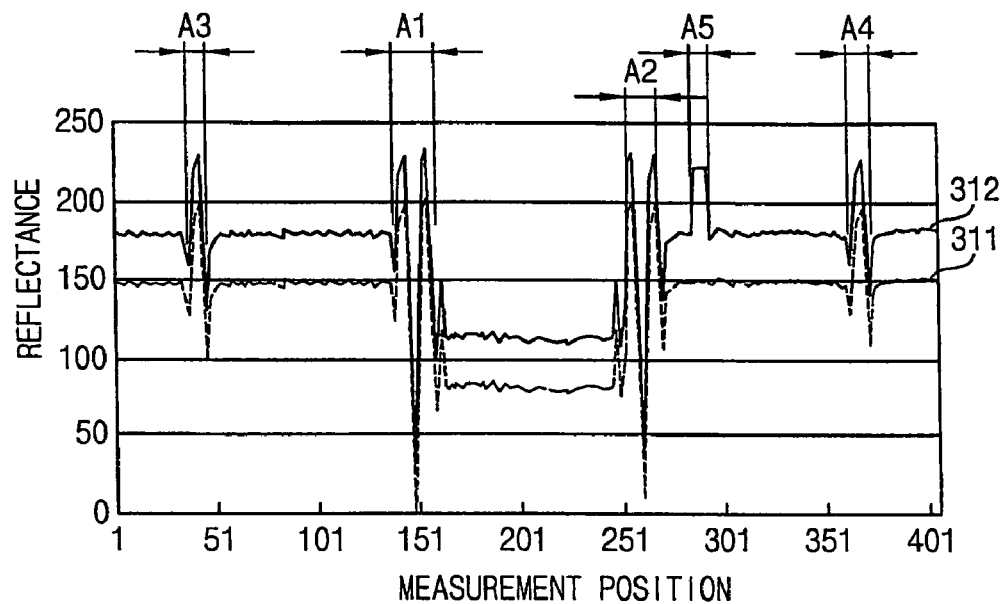
FIG. 6 is a graph showing the first and second reflection signals, which are generated from a light receiver shown in FIG. 2, with respect to a measurement position of the substrate.
Figure 7:
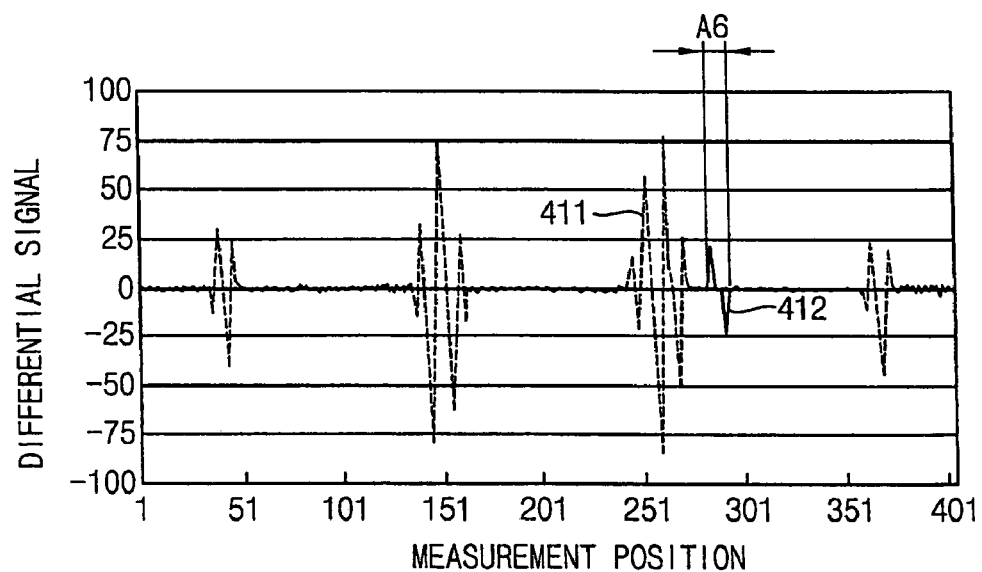
FIG. 7 is a graph showing the first and second differential signals generated in the differentiating operator shown in FIG. 2 with respect to a measurement position of the substrate.
Figure 8:
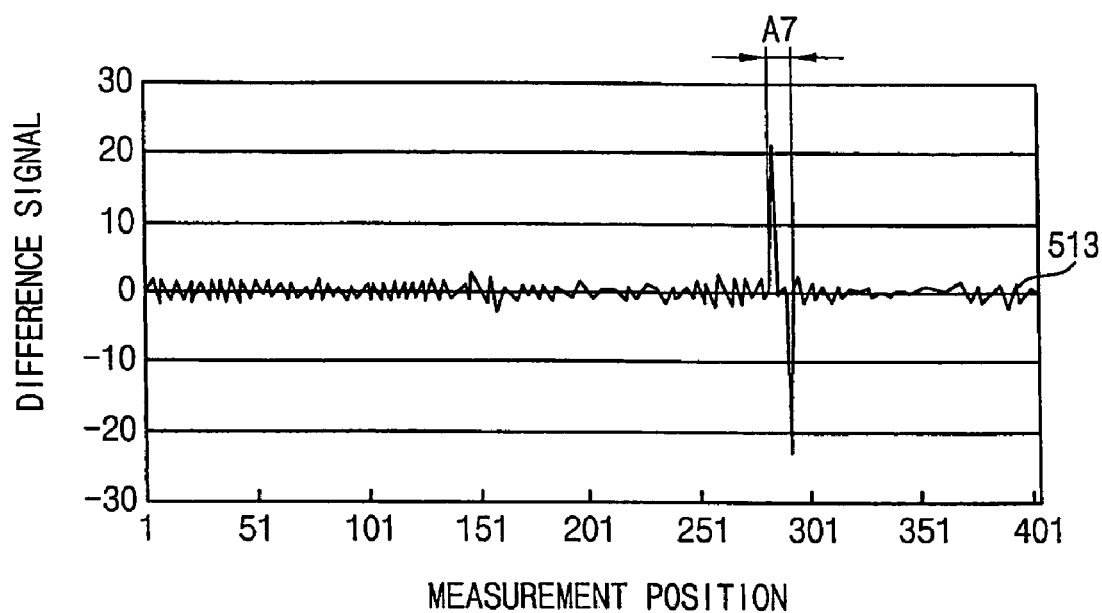
FIG. 8 is a graph showing a difference signal generated in a third processing module shown in FIG. 2 with respect to a measurement position of the substrate.

FIG. 5 is an enlarged image showing a substrate in FIG. 2, and FIG. 6 is a graph showing the first and second reflection signals, which are generated from the light receiver shown in FIG. 2, with respect to a measurement position of the substrate. FIG. 7 is a graph showing the first and second differential signals generated in the differentiating operator shown in FIG. 2 with respect to a measurement position of the substrate, and FIG. 8 is a graph showing the difference signal generated in the third processing module shown in FIG. 2 with respect to a measurement position of the substrate.

Referring to FIGS. 5 to 8, first and second dies 201 and 202 having the same shape are formed on the semiconductor wafer W. A scribe lane 210 is formed between the first and second dies 201 and 202. A plurality of cell regions 220 and peripheral regions 240 is repeatedly and periodically formed in each of the dies 201 and 202. As an example embodiment of the present invention, a particle 240 is formed on the cell region 220 of the first die 201. The particle 240 is formed on the cell region 220 to a predetermined volume after a thin layer is formed on the wafer W.

As shown in FIG. 5, the scribe lane 210 at a boundary portion of the dies 201 and 202 is brighter than the surrounding areas, and the boundary portions of the cell regions 220 and the peripheral regions 230 are distinguished from the surrounding areas in view of brightness. In addition, a boundary portion of the particle 240 is also distinguished from the surrounding areas thereof in view of brightness.

By merely viewing a surface appearance of the wafer W, one of ordinary skill in the art would reasonably expect that a reflectance of the reflected light reflected from the dies 201 and 202 may be different from that of the reflected light reflected from the scribe lane 210. In addition, one of ordinary skill in the art would also reasonably expect that the light irradiated onto the wafer W may be reflected from the scribe lane 210, a boundary portion of the cell regions 220, a boundary portion of the peripheral regions 230 and a boundary portion of the particle 240 at different reflectances, respectively. Practically, the light receiver 120 generates the reflection signal in accordance with an intensity of the reflected light received thereto when the light is irradiated on the wafer W in a first direction shown in FIG. 5.

In FIG. 6, the first light was irradiated onto the first-state wafer W at a spot size of about 1 μm and was reflected from the first-state wafer W, thereby generating the first reflection signal 311, and the second light substantially identical to the first light was irradiated onto the second-state wafer W and was reflected from the second-state wafer W, thereby generating the second reflection signal 312. Both the first and second reflection signals are shown in FIG. 6. That is, the first reflection signal 311 was generated from the bare wafer W, and the second reflection signal 312 was generated from the wafer W including the particle 240.

FIG. 6 shows that the second reflection signal 312 has a reflectance greater than that of the first reflection signal 311, which indicates that the reflectance of the light irradiated onto the wafer W may increase after the process for forming the thin layer on the wafer W.

FIGS. 5 and 6 show that the reflectances of the first and second reflected lights 311 and 312 are rapidly changed at some portions such as first, second, third, fourth and fifth portions thereof (A1, A2, A3, A4 and A5, respectively, in FIG. 6). The first and second portions A1 and A2 of the reflectances correspond to boundary lines 211 and 212 of the scribe lane 210, the third portion A3 of the reflectances corresponds to a first boundary portion 221 of the cell region 220, and the fourth portion A4 of the reflectances corresponds to a second boundary portion 222 of the cell region 220. The fifth portion A5 of the reflectances, which is only shown in the second reflectance light 312, corresponds to the particle 240.

The particle 240 and the position thereof on the wafer W may be detected by a comparison of the first and second reflection signals 311 and 312. However, the first and second reflection signals 311 and 312 in FIG. 6 are theoretical and idealistic, so that actual first and second reflection signals 311 and 312 are difficult to generate from an actual wafer. In practice, the second reflection signal 312 has the reflectance greater than that of the first reflection signal 311 from the actual wafer, and the first and second reflection signals 311 and 312 are continuously and delicately changed with respect to the measurement position of the actual wafer.

For the above reasons, the first and second reflection signals 311 and 312 are differentiated in the differentiating operator 130 so as to accurately detect the defect and the position thereof on the actual wafer. The differentiated signals of the first and second reflection signals 311 and 312 are shown in FIG. 7.

Referring to FIG. 7, a first differential signal 411 is generated by differentiating the first reflection signal 311, and a second differential signal 412 is generated by differentiating the second reflection signal 312.

The first processing module 145 extracts the peak points, which are substantially identical to one another, from the first and second differential signals 411 and 412, and the second processing module 150 overlaps the first and second differential signals 411 and 412 with respect to the extracted peak points, as shown in FIG. 7.

Referring to FIG. 7, most of the first and second differential signals 411 and 412 are overlapped with each other with high accuracy except for a sixth portion A6 of the differential signals, because the ground levels of the first and second differential signals 411 and 412 are substantially identical to each other and no variation potions of the first and second reflection signals 311 and 312 are substantially zero when differentiated. That is, the first and second differential signals 411 and 412 are substantially zero at the portions in which the first and second reflection signals 311 and 312 are not varied with respect to the measurement position.

The difference signal 513 shown in FIG. 8 is generated by subtracting the first differential signal 411 from the second differential signal 412, thereby more accurately ascertaining the difference between the first and second differential signals 411 and 412.

FIG. 8 shows that the second differential signal 412 is clearly different from the first differential signal 411 at a seventh portion A7. The seventh portion A7 in FIG. 8, the sixth portion A6 in FIG. 7 and the fifth portion A5 in FIG. 6 indicate the same position of the wafer W. That is, the wafer W is expected to include some defects at the portion designated by the seventh portion, the sixth portion A6 and the fifth portion A5.

The fourth processing module 160 locates positions of the portion 300 of the wafer W corresponding to the fifth portion A5, the sixth portion A6 and the seventh portion A7 by using a predetermined coordinate system. Thereafter, the actual position of the wafer W located in the fourth processing module 160 is re-inspected to confirm whether or not the processing defects are actually formed on the wafer W and to determine whether or not a subsequent process is to be performed on the wafer W. In the above process, the confirmation step that confirms whether the processing defects are actually formed on the wafer W may be optional under some processing conditions. The reliability of the inspection apparatus and the process of the present invention may be remarkably improved as compared with the conventional art, so that no additional steps for confirming the actual processing defects on the wafer W may be required.

Furthermore, an additional module may be added in which a defect size is calculated using the coordinates generated in the fourth processing module 160, and the processing defect is classified into some category based on the defect size. In this case, the processing defects are automatically detected and sorted in the inspection apparatus, so that manufacturing lines for semiconductor devices may be automatically controlled.

The above inspection apparatus 100 may be simplified as compared with a conventional inspection apparatus. In addition, the inspection process may be performed merely by using the reflected light that is reflected from the wafer at the same angle as the incident angle, so that the reflected light may be received into the light receiver while the wafer W rotates at a high velocity. As a result, the inspection apparatus 100 may be structured into a slim shape, such as that similar to a compact disc player.

According to the example embodiments of the present invention, the first reflection signal generated from a bare substrate and the second reflection signal generated from a processed substrate are differentiated, respectively, to thereby generate first and second differential signals. Then, the first and second differential signals are compared with each other, and the processing defects on the processed wafer may be accurately detected based on the results of the comparison of the first and second differential signals. In addition, the inspection apparatus of the present invention may only utilize the reflected light that reflected from the processed substrate at a reflection angle substantially identical to an incident angle except for the light scattered from the processed substrate, so that the inspection process may be performed in a shorter time period. As a result, the processed wafer may be inspected with high efficiency and with high reliability. Further, the re-inspection on the defected portion of the processed wafer may not be required, so that manufacturing costs may be reduced by as much as the re-inspection cost. Furthermore, the re-inspection process may be automatically performed in the above inspection apparatus, so that the number of manual operations is reduced, to thereby reduce operation costs for the inspection apparatus.

Although the example embodiments of the present invention have been described, it is understood that the present invention should not be limited to these example embodiments but various changes and modifications can be made by one skilled in the art within the spirit and scope of the present invention as hereinafter claimed.

What is claimed is:

1. A method of inspecting an object, comprising:
scanning a bare object using a first light, the bare object including no structures thereon;
receiving a first reflection signal that is reflected from the object;
performing a process on the object, so that a structure is formed on the object;
scanning the processed object using a second light;
receiving a second reflection signal that is reflected from the processed object;
generating first and second differential signals by respectively differentiating the first and second reflection signals; and
detecting a processing defect on the processed object by a comparison between the first and second differential signals,
wherein detecting the processing defect includes:
overlapping the first and second differential signals;

detecting at least one signal-deviation portion in which the first and second differential signals are spaced apart out of an allowable error range; and locating a portion of the processed object corresponding to the signal-deviation portion.

2. The method of claim 1, wherein the first and second differential signals overlap each other on a basis of peak points of the first and second differential signals, the peak points being substantially identical to one another in the first and second differential signals.

3. The method of claim 1, wherein the first reflection signal includes an intensity of the first reflected light and the second reflection signal includes an intensity of the second reflected light.

4. The method of claim 1, wherein the first and second lights have the same incident angle with respect to the bare substrate and the processed object, respectively.

5. The method of claim 4, wherein the incident angle is in a range from about 10° to about 90° with respect to a surface of the processed object.

6. The method of claim 1, wherein the object includes a semiconductor substrate and processing the object includes forming a minute structure on the semiconductor substrate.

7. An apparatus for inspecting an object, comprising:
- a light source for irradiating a first light onto a bare object and for irradiating a second light onto a processed object, the bare object including no structures thereon and the processed object including structures thereon;
- a light receiver for receiving first and second reflection signals reflected from the bare object and the processed object, respectively;
- a differentiation operator for generating first and second differential signals by differentiating the first and second reflection signals; and
- a detector for detecting a processing defect on the processed object by a comparison between the first and second differential signals, wherein the detector includes:
- a first processing module for detecting peak points in the first and second differential signals, the peak points being substantially identical to one another in the first and second differential signals;
- a second processing module for overlapping the first and second differential signals on a basis of the detected peak points;
- a third processing module for detecting at least one signal-deviation portion in which the first and second differential signals are spaced apart out of an allowable error range; and
- a fourth processing module for locating a portion of the processed object corresponding to the signal-deviation portion.

8. The apparatus of claim 7, further comprising a memory unit for storing the first and second differential signals.

9. The apparatus of claim 7, wherein the light source and the light receiver positions are disposed parallel with each other in a direction vertical to the object, so that the first and second lights are vertically irradiated onto the bare and processed objects, respectively, and the first and second reflection signals are also vertically received into the light receiver, respectively.

10. The apparatus of claim 7, wherein the light receiver includes a photo multiplier tube, a photodiode, a phototransistor and a photoelectric tube.

11. The apparatus of claim 7, wherein the object includes a semiconductor substrate including a plurality of dies.

* * * * *